United States Patent
Sacchetti

(10) Patent No.: US 12,023,358 B2
(45) Date of Patent: Jul. 2, 2024

(54) CATALYST FOR THE REGENERATION OF TISSUES AND RELATED METHOD FOR MAKING IT

(71) Applicant: GENLIFE SAGL, Paradiso (CH)

(72) Inventor: Benedetto Sacchetti, Sonnino (IT)

(73) Assignee: GENLIFE SAGL, Paradiso (CH)

(*) Notice: Subject to any disclaimer, the term of this patent is extended or adjusted under 35 U.S.C. 154(b) by 0 days.

(21) Appl. No.: 16/645,911

(22) PCT Filed: Sep. 12, 2018

(86) PCT No.: PCT/IB2018/001077
§ 371 (c)(1),
(2) Date: Mar. 10, 2020

(87) PCT Pub. No.: WO2019/053503
PCT Pub. Date: Mar. 21, 2019

(65) Prior Publication Data
US 2020/0276245 A1 Sep. 3, 2020

(30) Foreign Application Priority Data
Sep. 14, 2017 (IT) .................. 102017000102994

(51) Int. Cl.
*A61K 35/35* (2015.01)
*A61K 9/19* (2006.01)
*A61K 38/20* (2006.01)

(52) U.S. Cl.
CPC ............. *A61K 35/35* (2013.01); *A61K 9/19* (2013.01); *A61K 38/2026* (2013.01); *A61K 38/204* (2013.01); *A61K 38/2066* (2013.01)

(58) Field of Classification Search
None
See application file for complete search history.

(56) References Cited

U.S. PATENT DOCUMENTS

| | | | |
|---|---|---|---|
| 9,056,084 B2 * | 6/2015 | Ylikomi | A61K 38/1825 |
| 9,730,964 B2 * | 8/2017 | Vesey | A61P 17/10 |
| 2015/0209390 A1 | 7/2015 | Chu et al. | |
| 2017/0128628 A1 * | 5/2017 | Hiles | A61L 27/24 |

FOREIGN PATENT DOCUMENTS

| | | | | |
|---|---|---|---|---|
| CN | 107034183 A | 8/2017 | | |
| KR | 20150088374 A | 8/2015 | | |
| RU | 2574017 C1 | 1/2016 | | |
| WO | WO-2007037572 A1 * | 4/2007 | ............. | A61K 35/35 |
| WO | 2010026299 A1 | 3/2010 | | |
| WO | 2016015767 A1 | 2/2016 | | |
| WO | 2017139795 A1 | 8/2017 | | |

OTHER PUBLICATIONS

Kim, W., et al. Wound healing effect of adipose-derived stem cells: a critical role of secretory factors on human dermal fibroblasts. Journal of Dermatological Science 48, pp. 15-24, 2007 (Year: 2007).*
Blaber, S. et al., Analysis of in vitro secretion profiles from adipose-derived cell populations. Journal of Translational Medicine, 10(172), 16 pages, 2012 (Year: 2012).*
Allen, T. H., et al., Density, fat, water and solids in freshly isolated tissues. Journal of Applied Physiology, 14, pp. 1005-1008 Nov. 1959 (Year: 1959).*
Nakamura, S., et al. Increased survival of free fat grafts and vascularization in rats with local delivery of fragmin/protamine microparticles containing FGF-2 (F/P MP-F). Journal Of Biomedical Materials Research B: Applied Biomaterials, 96B(2), pp. 234-241, Feb. 2011 (Year: 2011).*
Ballak, D., et al. IL-1 family members in the pathogenesis and treatment of metabolic disease: Focus on adipose tissue inflammation and insulin resistance. Cytokine, 75(2) pp. 280-290 Jul. 17, 2015 (Year: 2015).*
Wensveen, F., et al. The "Big Bang" in obese fat: events initiating obesity-induced adipose tissue inflammation. European Journal of Immunology, 45(9) pp. 2446-2456, 2015 (Year: 2015).*
Fantuzzi, G. Adipose tissue, adipokines, and inflammation. Molecular mechanisms in allergy and clinical immunology, 115(5), pp. 911-919, May 2005 (Year: 2005).*
Guillaume-Jugnot, P., et al. State of the art. Autologous fat graft and adipose tissue-derived stromal vascular fraction injection for hand therapy in systemic sclerosis patients. Current Research in Translational Medicine, 64, pp. 35-42, 2016 (Year: 2016).*
Kim, W., et al. The pivotal role of PDGF and its receptor isoforms in adipose-derived stem cells. Histology and Histopathology, 30(7) Jul. 2015 (Year: 2015).*
Hauner, H., et al. Cultures of human adipose precursor cells. Methods in Molecular Biology, 155: Adipose Tissue Protocols, pp. 239-247, 2001 (Year: 2001).*

(Continued)

*Primary Examiner* — Elly-Gerald Stoica
(74) *Attorney, Agent, or Firm* — Silvia Salvadori, P.C.; Silvia Salvadori

(57) ABSTRACT

A biological catalyst for the regeneration of tissues, obtainable directly from an adipose starting material, includes adipose material in liquid solution in a quantity of between 1.0 and 1.5 grams per millilitre of adipose starting material, in which a quantity of between 2 and 30 milligrams of proteins is present, said proteins comprising at least: from 0 to 60 picograms of PDGF, from 300 to 1300 picograms of VEGF, from 10 to 100 picograms of TGFb1, from 3000 to 7500 picograms of FGFb, from 400 to 4000 picograms of IL-1 RA. The biological catalyst is obtained from a method including at least the steps of collecting an adipose starting material; centrifuging the adipose material, to separate the collected material at least into an oily fraction, an aqueous fraction and a cellular fraction; removing the surface oily fraction; collecting the aqueous fraction and the cellular fraction, in which the above-mentioned proteins are found.

11 Claims, 4 Drawing Sheets

(56) References Cited

OTHER PUBLICATIONS

Islam et al., A review of macroscale and microscale cell lysis methods, Micromachines, 8, 83, 2017. (Year: 2017).*
Semenzato et al. A novel benchtop device for efficient and simple purification of cytokines, growth factors and stem cells from adipose tissue. Biomedicines 11, 1006, 2023. (Year: 2023).*
Sarkanen J. R. et al: "Human adipose tissue extract induces angiogenesis and adipogenesis in vitro", Tissue Engineering, Part A, Mary Ann Liebert, Inc., Publishers, US, vol. 18, No. 1-2, Jan. 1, 2012, pp. 17-25.
Lu Zijing et al: "Adipose tissue extract promotes adipose tissue regeneration in an adipose tissue engineering chamber model", Cell and Tissue Research, Springer, DE, vol. 364, No. 2, Dec. 17, 2015, pp. 289-298.
International Search Report and Written Opinion dated Apr. 12, 2019 for counterpart International Application No. PCT/IB2018/001077.
C.E. Juge-Aubry et al: "Adipose tissue Is a Major Source of Interleukin-1 Receptor Antagonist; Upregulation in Obesity and Inflammation", Diabetes, vol. 52, No. 5, May 1, 2003, pp. 1104-1110, XP055001835, ISSN: 0012-1797, DOI: 10.2337/diabetes.52.5.1104.
Celprogen: "Data Sheet Human Adipose Derived Stem Cell Condition Media-Lyophilized—100kg Catalog No. M36010-11CM-100kg Description: Human Adipose Derived Stem Cell Conditioned Media, lyophilized Sterile Filtered and tested with Human Adipose Derived Stem Cells in Culture", Jan. 1, 2015, XPo55365348, Celprogem Website, URL: http://www.celprogen.com/uploads/product/14474379382.pdf.

* cited by examiner

CATALYST FOR THE REGENERATION OF TISSUES AND RELATED METHOD FOR MAKING IT

This application is the National Phase of International Application PCT/I62018/001077 filed Sep. 12, 2018 which designated the U.S.

This application claims priority to Italian Patent Application No. 102017000102994 filed Sep. 14, 2017, which application is incorporated by reference herein.

TECHNICAL FIELD

This invention relates to a catalyst for the regeneration of tissues and the related method for making it. It consists of a compound comprising cytokines, growth factors, stimulation factors and chemotactic factors, taken and isolated from adipose materials, usable for the treatment of lesions, for the reconstruction and repair of tissue damage, in many fields of medicine, for example dermatology, orthopaedics, plastic surgery, vulnology, dentistry, ophthalmology, urology, veterinary medicine.

In the event of a wound or lesion, a tissue begins a natural biological repair phenomenon. The damaged tissue is therefore reconstructed and the damage repaired. The repair process is characterised by cellular proliferation of the epithelial, endothelial and connective structures present on the edges of the lesion. In the regeneration of epithelial tissues, the process is characterised by the proliferation of fibroblasts, cellular elements which secrete hyaluronic acid, an active component in the formation of collagen fibres, whose activity will last for the time necessary for the collagen produced to fill the wound. Simultaneously with the step just described, the proliferation of the cells of the basal layer of the epithelium begins. This tissue has the important function of covering the wound.

Even in phenomena known as "photoaging", dermatological manifestations (for example wrinkles, melanic patches, epidermal thickening) of biochemical phenomena involving the cells and tissue structures, both surface and deep, of the skin correspond to lesions sustained from structural alterations of the cells and of the dermal tissue unleashed by attacks from free radicals mainly produced by the triggering action of UV radiation and to a lesser extent by cellular metabolism.

In fact, even gradual loss of anabolic activity by fibroblasts, the cells responsible for the regeneration of collagen and elastic proteins and of the dermal extracellular matrix, and the proportional increase in catabolic activity contribute to tissue degradation. Faced with an insufficient or reduced synthesis of new dermal structural proteins and of hydrophilic extracellular matrix, there is an increase in their degradation by specific catabolic enzymes (known as metalloproteinases, collagenases, elastases and various proteases) which, by synthesising more than fibroblasts, cause an inexorable alteration of the dermal tissue which therefore becomes less solid (skin laxity), less hydrated (reduced quantity of glycosaminoglycans and proteoglycans) and above all less elastic (reduced collagen regeneration).

Such alterations produce at a surface level a series of aesthetic imperfections which are often the cause of strong psychological uneasiness.

BACKGROUND ART

In all branches of medicine involving the need for repairing tissue damage, the problem is dealt with according to two guidelines which, in practical cases, may be followed together or as alternatives to one another: the first consists of use of therapies involving stem cells, the second consists of the use of reconstructive or filling "fillers", such as hyaluronic acid and collagen.

The therapeutic action of stem cells may be traceable to two mechanisms: stem cell differentiation into resident cells and the release of regenerative trophic factors by the stem cells. The respective contributions of these two mechanisms are still to be clarified, although it has been theorised that it is not just stem cells which become mature cells of the injured tissue, but that they also release factors stimulating this tissue, which can therefore start proliferating and differentiating again, thereby regenerating.

However, stem cell therapy has many problems linked not just to costs, technical and application difficulties and regulatory complications, but also to ethical and religious scruples. Moreover, stem cell therapy is only possible by injection or, in some cases, topically, and not orally. Moreover, although the supernatant of the stem cell in culture contains growth factors, cytokines, chemotactic factors, which are believed to be responsible for the beneficial effect of stem cell therapy on tissue growth and/or repair, any use of active factors which can be isolated from the supernatant of the stem cells has not just the same ethical problems as use of the stem cells themselves, but also very high costs.

With regard to that, Chinese patent CN107034183A is known, which covers a method for obtaining a freeze-dried extract containing peptide-protein components, otherwise known as growth factors, from the laboratory processing of a material of adipose origin to which exogenous biochemical products are added (for example, proteolytic enzymes) in such a way as to separate a cellular fraction of the starting material and from it obtain a supernatant solution from the "in vitro" culture of stem cells.

It should be emphasised that the growth factors useful for tissue regeneration therapies must have a concentration above a predetermined level. For example, FGFb, a biomolecular component with trophic-stimulant action, has excellent prospects for use as a regenerating supplement in the many clinical sectors requiring the regeneration of fibrous connective tissues.

However, various therapeutic studies have demonstrated that FGFb is only really effective when it has a high concentration on the target tissues, of at least nanograms per millilitre. In that sense, the quantity of FGFb, and more generally of various growth factors, obtainable by means of the method described in CN107034183A is ineffective when removing a tolerable quantity of adipose material; vice versa, to obtain therapeutically effective quantities of FGFb, it would be necessary to collect enormous quantities of adipose material.

Nowadays, surgery combats the effects of trauma, lesions, and other histological alterations even with the use of reconstructive/filling "fillers". For example, plastic surgery limits the effects of ageing using various non-invasive methods, such as by augmenting the soft tissue of the face, and of other parts of the body, using filler. A large number of fillers are available to buy, each with its own chemical components, recommended uses and effectiveness. Collagen implants, whether derived from animals or people, have been used for some time for soft tissue augmentation. Bovine collagen-based fillers were the most popular injectable implants in the final two decades of the last century. Subsequently bio-engineered human collagen-based products became available in addition to fillers containing hyaluronic acid.

Fillers containing hyaluronic acid are the preferred products for soft tissue augmentation: they last longer, are less immunogenic and can be disaggregated by hyaluronidase. For these reasons hyaluronic acid-based fillers are the most common nowadays. However, the injection of hyaluronic acid-based fillers may result in either immediate or delayed complications, which can range from mild to severe. Recent years have seen the spread of use of chemically modified hyaluronic acid-based fillers, but all of the fillers currently available can induce adverse reactions. Substances which are quickly biodegradable and reabsorbable may, for example, cause serious complications, but they usually spontaneously disappear within the space of a few months. In contrast, fillers with a slower biodegradability and which are not reabsorbable may cause a rise in severe reactions with a minimal or null tendency to spontaneously resolve. These reactions may even occur many years after injection. Therefore, there is a need for new fillers which do not have the above-mentioned disadvantages but which promote a regenerating and trophic action.

Even in the field of inflammatory rheumatic diseases, psoriatic disease and osteoarthritis, in recent decades there has been increasing use of therapies based on the administration of biological medicines containing cytokines.

Since in such pathologies the production of certain inflammatory protein molecules was observed, some of them identified with the acronyms IL-6, IL-1, TNFa, IL-4, the therapies based on the use of cytokines followed two routes: administration of anti-inflammatory cytokines and inhibition of pro-inflammatory cytokines.

Amongst the above-mentioned molecules, IL-1 and in particular IL-1 b play an important role in the onset of such diseases; there is a natural inhibitor of the receptor of those molecules, known as IL-1 RA, which, in order to be able to act effectively, must be 10 to 100 times in excess of IL-1 b: although IL-1 RA is endogenously produced, it cannot reach the quantities necessary for countering the pro-inflammatory action of IL-1b, which means that the possibility of exogenously administering it would be a precious therapeutic opportunity.

DISCLOSURE OF THE INVENTION

The aim of this invention is, therefore, to eliminate the above-mentioned disadvantages. It has been discovered that the body fluids and some tissues of mammals contain the same active factors as are released by stem cells and therefore present in the supernatant of stem cell cultures. One of the sources of these factors is fat. Therefore, the invention, characterised by the claims, achieves the aim by means of a compound containing growth factors, cytokines and chemotactic factors, obtained from adipose materials for cellular stimulation aimed at regenerating tissues.

The main advantage obtained by means of this invention basically consists of the fact that the substances which are part of the compound are associated in a form such that it increases the bio-availability of every single active ingredient and therefore improves its effectiveness once introduced into common techniques and forms of use.

A further advantage is the fact that the substances contained in the invention increase the replication and anabolic activity of the cells of the injured tissues (in particular, connective stromal elements, keratinocytes and fibroblasts), improve cutaneous trophism by exercising a regenerating action on the dermal-epidermal tissue, promote cellular differentiation and promote the synthesis of macromolecules such as extracellular structural proteins, for example collagen, elastin and fibronectin, and proteoglycans and glycosaminoglycans such as hyaluronic acid.

Moreover, the substances contained in the invention demonstrate a significant anti-inflammatory action, accompanied by a modest presence of pro-inflammatory substances.

The invention also has a degree of penetration of the dermal layer of the skin which is much greater than that of prior art creams and emulsions which use the same substances, and therefore a greater quantity of it reaches the aqueous medium where it spreads and carries out its biological actions at a cellular level.

The invention may advantageously be associated with supports, constituted of bio-material, for the treatment of tissue lesions, both with wounds, contributing to the healing process, and when subjected to radiation treatments, acting to prevent and limit any damage caused by the radiation itself.

Therefore, collection of biological material necessary is moderately invasive and its treatment does not require the addition of exogenous chemical or bio-chemical additives (such as proteolytic enzymes), but is based on spontaneous activation of the various cellular and tissue components thanks to the production and release of factors involved in the regeneration and remedy process.

The minimal manipulation of this material involves the use of only physical procedures, allowing the application of a simpler regulatory procedure, even more so if the manipulation is on the same origin tissue.

Finally, the invention, obtained in an aqueous solution, can be easily freeze-dried and preserved at suitable temperatures (between 4° C. and −20° C.) until it is used: this prolongs the stability of the active ingredient, allows the doctor to decide the most appropriate concentration for it, increases the preservation time (even for up to 2 years) and simplifies its storage.

BRIEF DESCRIPTION OF THE DRAWINGS

Further advantages and features of the invention are more apparent in the detailed description which follows, with reference to the accompanying drawings, in which.

DETAILED DESCRIPTION OF PREFERRED EMBODIMENTS OF THE INVENTION

The invention consists of a biological catalyst for the regeneration of tissues, directly obtainable (that is to say, without any biological manipulation, in English "enzyme free") from an adipose starting material (1). In fact, it was observed that the adipose material of many mammals contains, chiefly in the form of proteins, most of the active factors released by stem cells, and therefore also traceable in the supernatant of stem cell cultures.

By means of a method described below, a biological catalyst 10 is obtained, comprising adipose material in a liquid solution in a quantity of between 1.0 and 1.5 grams per millilitre of adipose starting material 1, containing a 2 to 30 milligram quantity of proteins. Those proteins comprise at least: from 0 to 60 picograms of PDGF, from 300 to 1300 picograms of VEGF, from 10 to 100 picograms of TGFb1, from 3000 to 7500 picograms of FGFb.

The acronyms used identify proteins which are particularly active in the repair of tissue damage, and in particular they stand for: PDGF (Platelet derived growth factor) a protein which regulates growth and differentiation of cells of mesodermal origin; VEGF (Vascular endothelial growth factor) a protein which regulates the growth of endothelial cells and angiogenesis; TGFb1 (Transforming growth factor b1) regulates growth, differentiation, adhesion, migration and other cellular functions; FGFb (Fibroblast growth factor b) regulates growth and differentiation of cells of mesenchymal origin.

Figure 2:
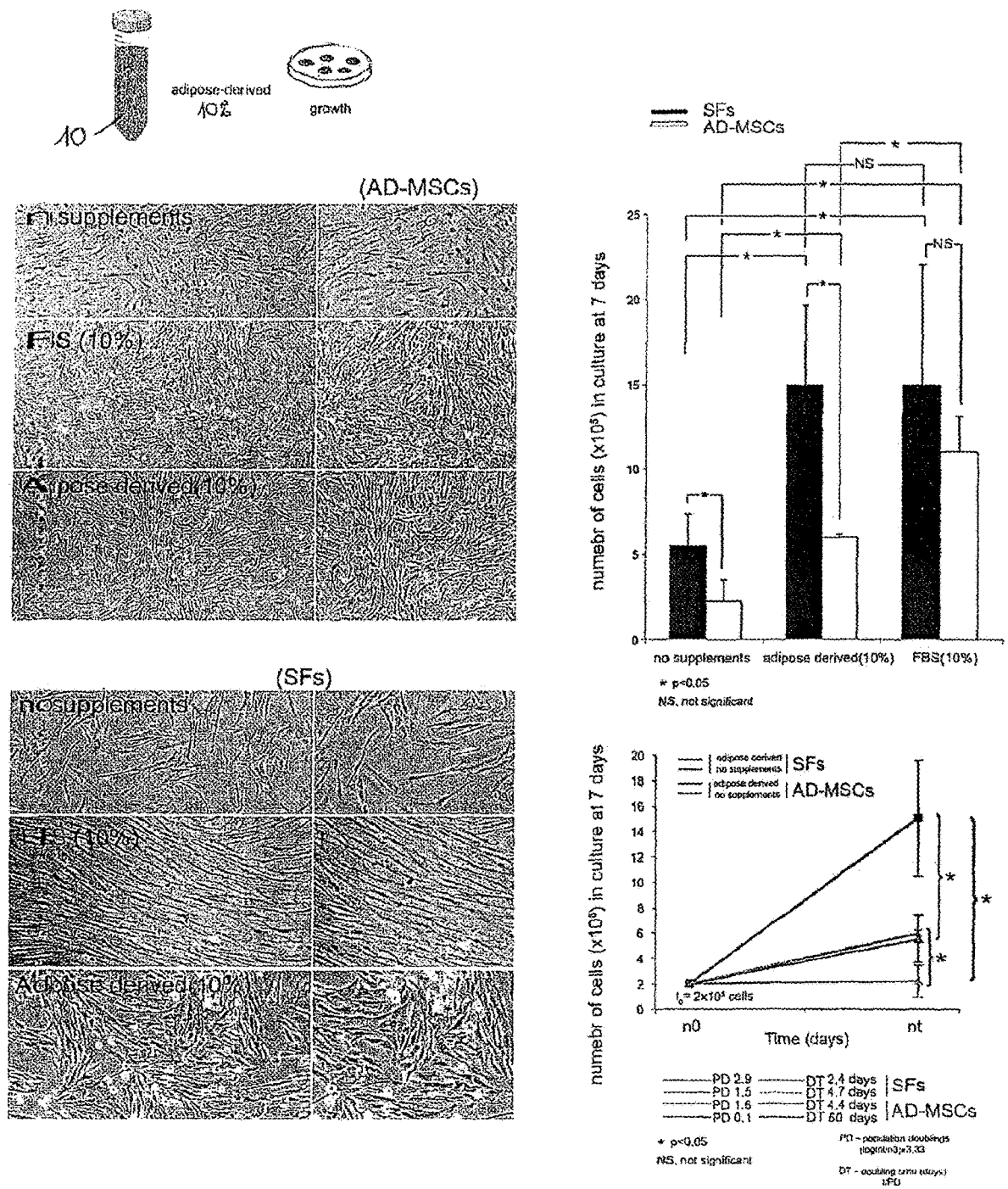
FIGS. 2 and 3 show the results of "in vitro" tests of the invention.

The "in vitro" and "in vivo" tests demonstrate the effectiveness of this product, confirming the stimulating action of the invention on various cellular components of tissues. In fact, as shown in FIG. 2, use of the invention at a 10% concentration (Adipose Derived 10%) increased the proliferation capacity of mesenchymal stromal cells derived from human adipose tissue (AD-MSCs) and of dermal fibroblasts (SFs), relative to the controls in which the same cells have traditionally been supported using fetal bovine serum at a 10% concentration (FBS10%), or in the absence of supplements (no supplements).

Figure 3:
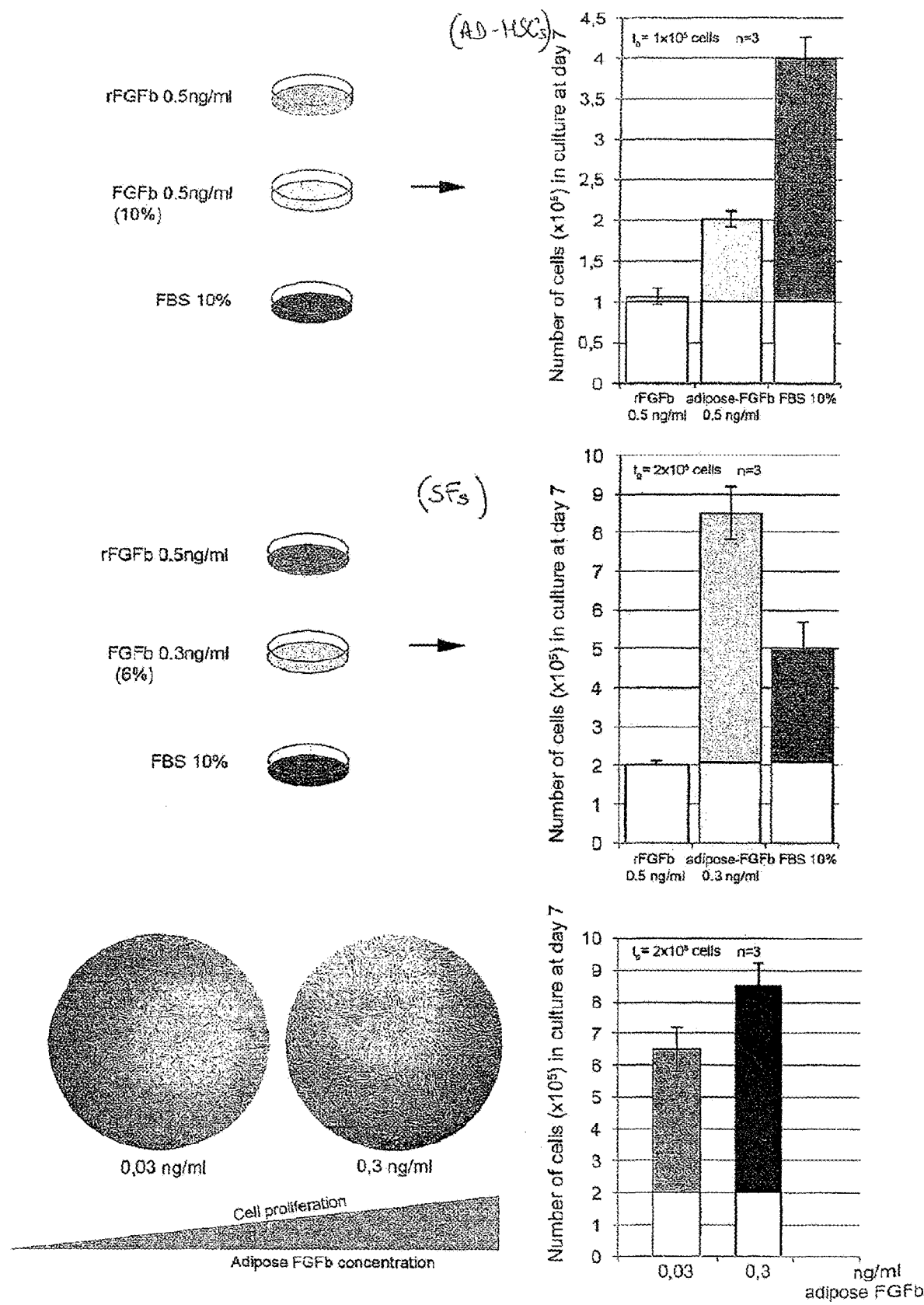

A further test of the effectiveness of this product is shown in FIG. 3, which illustrates how use of the invention, at a concentration of 6 and 10%, and containing a quantity of FGFb respectively of 0.3 ng/ml and 0.5 ng/ml, increased the proliferation capacity of mesenchymal stromal cells derived from human adipose tissue (AD-MSCs) and of dermal fibroblasts (SFs) relative to the same cells in the presence of recombinant FGFb (rFGFb) used at the concentration of 0.5 ng/ml.

Figure 4:
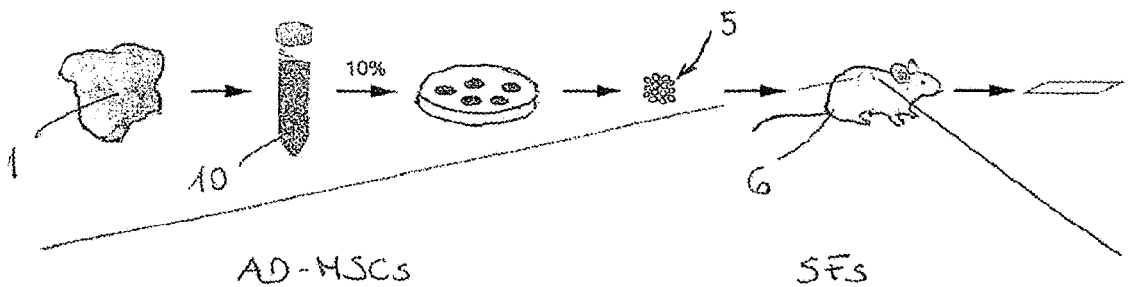
FIG. 4 shows the results of "in vivo" tests of the invention.
Figure 4:
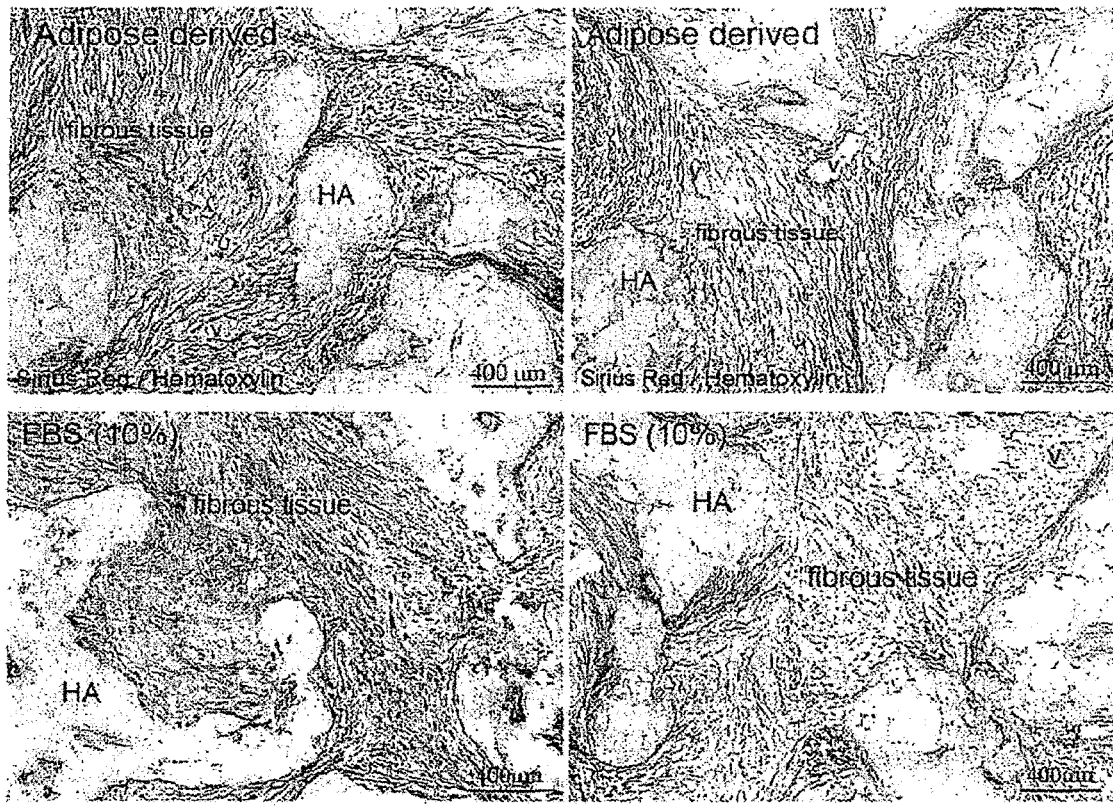
Figure 4:
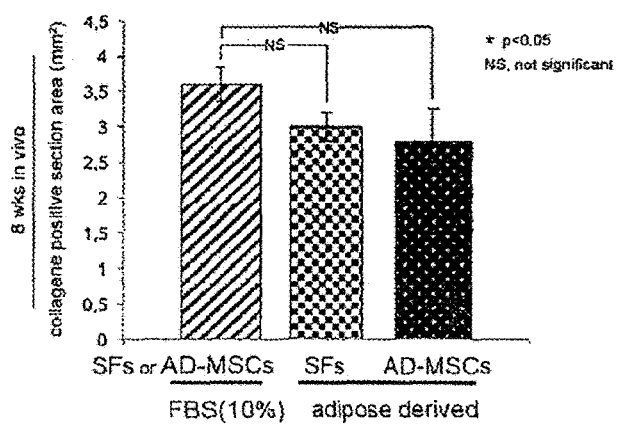

FIG. 4 shows how experiments conducted on mice 6, which were given subcutaneous grafts of the invention on an amorphous support 5, after an eight week interval resulted in a considerable cellular and vascular proliferation with abundant formation of collagen fibres.

Moreover, the above-mentioned proteins also comprise many molecules characterised by a strong anti-inflammatory action, accompanied by a rather small quantity of pro-inflammatory molecules.

In particular, they contain at least: from 400 to 4000 picograms of IL-1 RA, a strong inhibitor of the receptor of the inflammatory molecule IL-1b, from 1 to 40 picograms of IL-4 and from 0.5 to 5 of IL-10, which are interleukins with a strong anti-inflammatory action.

On the other hand, the same proteins only contain: from 0.5 to 10 picograms of IL-1b, the inflammatory protein opposed by IL-1RA, from 1 to 10 picograms of TNFa, also known as tumour necrosis factor, and from 5 to 500 picograms of IL-6, an interleukin with pro-inflammatory action.

It is obvious that topical administration of the invention with such high quantities of IL-1 RA allows a local availability of this cytokine at concentrations such that it performs its biological action at cellular level and effectively opposes the inflammatory diseases which the patient treated suffers from.

Figure 1:
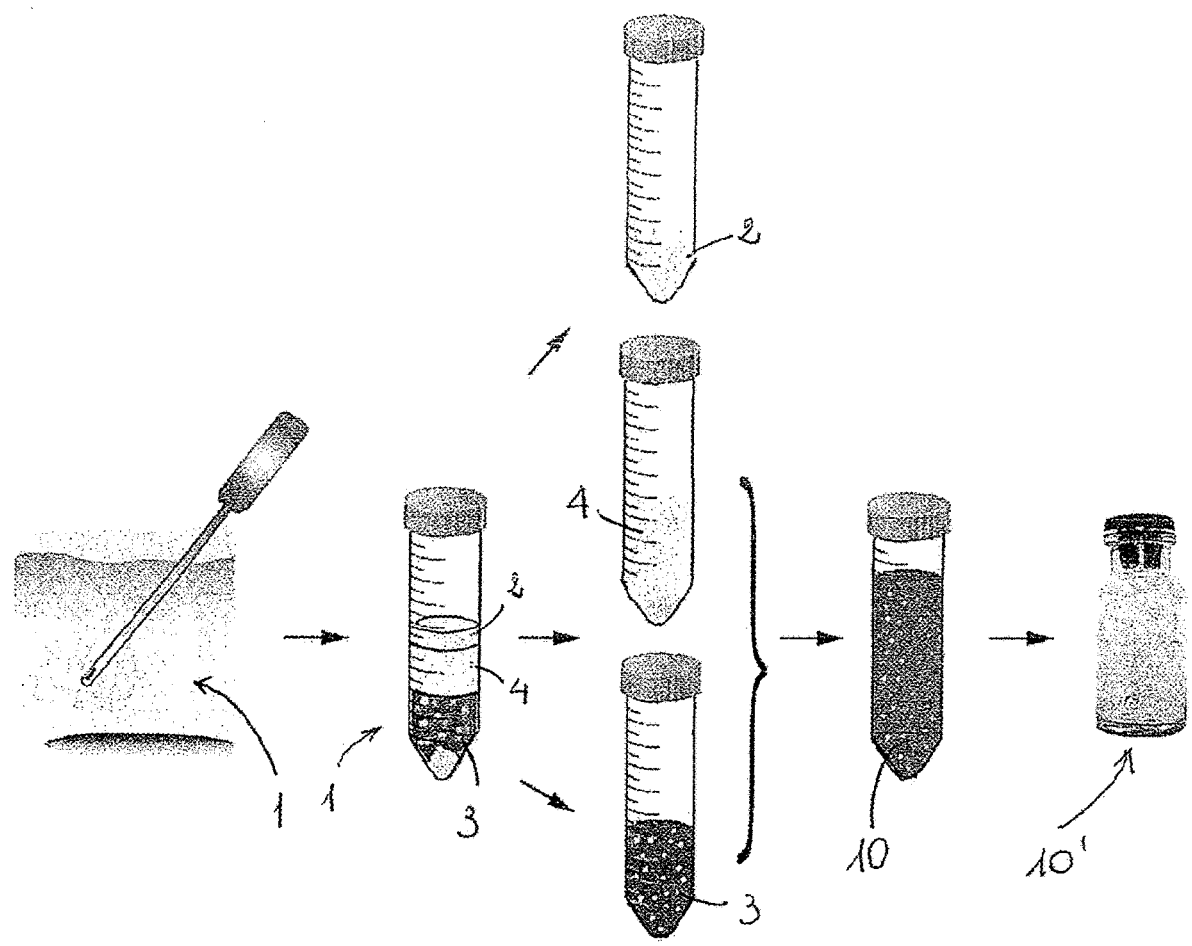
FIG. 1 is a schematic illustration of the basic steps of the method used to obtain the invention.

The method for obtaining the biological catalyst for the regeneration of tissues described above, schematically illustrated in FIG. 1, comprises first collecting an adipose starting material 1: that starting material could even be the result, for example, of liposuction performed on the same patient who is to be treated with the invention.

The adipose material 1 collected is centrifuged at least once, for separating the collected material at least into an oily fraction 2, an aqueous fraction 3 and a cellular fraction 4; since the active factors useful for the regeneration of tissues are mainly in the aqueous fraction 3 and to a certain degree in the cellular fraction 4, the surface oily fraction 2 is removed, whilst the aqueous fraction is separated from the cellular fraction 4.

Because the aqueous fraction 3 contains the most active ingredients, it is already suitable for use as a biological catalyst 10 for the regeneration of tissues. However, a better result can be achieved, by further processing the cellular fraction 4: in this case, first the cellular fraction 4 is broken up, and then it is centrifuged at least once and the surface oily fraction is subsequently removed. At this point, the supernatant aqueous solution is collected and added to the aqueous fraction 3 previously obtained.

In any case, the aqueous fraction which is obtained is subsequently filtered, to eliminate any tissue and cellular debris, as well as to remove a possible microbial contamination, and preferably frozen.

Before or after freezing, it is possible to proceed with dehydration of the aqueous fraction 3, in such a way as to obtain the biological catalyst in freeze-dried form 10': in fact, in this form the stability of the active ingredients is extended, preservation is facilitated and, at the moment of use, it can be diluted within a wide range depending on the needs of the patient.

The invention claimed is:

1. A biological catalyst for the regeneration of tissues, obtainable from a mammalian adipose starting material, wherein the biological catalyst comprises adipose material in liquid solution in a quantity of between 1.0 and 1.5 grams per milliliter of adipose starting material, comprising of 2-30 mg of proteins in which at least 400-4000 pg of IL-IRA and an IL-1b receptor and further at most 5-500 pg of IL-6, 1-10 pg of TNFα, 0.5-10 pg of IL-1b are present and wherein the biological catalyst is obtained by a process comprising:
   collecting the mammalian adipose starting material;
   centrifuging the mammalian adipose starting material at least once, to separate at least into an oily fraction, an aqueous fraction and a cellular fraction;
   removing the oily fraction;
   collecting the aqueous fraction separated from the cellular fraction and wherein the above steps are accomplished without the addition of enzymes.

2. The biological catalyst according to claim 1, wherein 1 to 40 picograms of IL-4 and 0.5 to 5 picograms of IL-10, are present in the biological catalyst.

3. A method for obtaining a biological catalyst for regeneration of tissues, comprising the following steps:
   collecting a mammalian adipose starting material;
   centrifuging the mammalian adipose starting material at least once, to separate at least into an oily fraction, an aqueous fraction and a cellular fraction;
   removing the oily fraction;
   collecting the aqueous fraction separated from the cellular fraction, wherein the above steps are accomplished without the addition of enzymes, and wherein the biological catalyst comprises adipose material in liquid solution in a quantity of between 1.0 and 1.5 grams per milliliter of adipose starting material, comprising of 2-30 mg of proteins in which at least 400-4000 pg of IL-IRA and an IL-1b receptor and further at most 5-500 pg of IL-6, 1-10 pg of TNFα, 0.5-10 pg of IL-1b are present.

4. The method according to claim 3, wherein the cellular fraction is treated according to the following steps:
   breaking down the cellular fraction;
   centrifuging;
   removing the oily fraction;
   collecting the supernatant aqueous solution;

adding the supernatant aqueous solution to the aqueous fraction.

5. The method according to claim 3, and further comprising at least one subsequent step of filtering the aqueous fraction.

6. The method according to claim 3, and further comprising a subsequent step of freezing the aqueous fraction.

7. The method according to claim 3, and further comprising a further step of dehydrating the aqueous fraction, in such a way as to obtain the biological catalyst in freeze-dried form.

8. The biological catalyst according to claim 1, and further comprising freeze-dried adipose material.

9. The biological catalyst according to claim 1, wherein:
the mammalian adipose starting material is obtained from a surgical procedure.

10. The biological catalyst according to claim 1, wherein:
the mammalian adipose starting material is obtained from a liposuction procedure.

11. The biological catalyst according to claim 3, wherein:
the mammalian adipose starting material is obtained from a surgical procedure.

* * * * *